United States Patent [19]

Ohtsuka

[11] Patent Number: 5,572,266
[45] Date of Patent: Nov. 5, 1996

[54] FUNDUS CAMERA

[75] Inventor: Hiroyuki Ohtsuka, Tokyo, Japan

[73] Assignee: Kabushiki Kaisha Topcon, Tokyo, Japan

[21] Appl. No.: 280,198

[22] Filed: Jul. 25, 1994

[30] Foreign Application Priority Data

Jul. 26, 1993 [JP] Japan .................................. 5-183933

[51] Int. Cl.$^6$ .................................................. G03B 29/00
[52] U.S. Cl. ............................................ 396/18; 351/208
[58] Field of Search ....................... 354/62; 351/206–208

[56] References Cited

U.S. PATENT DOCUMENTS

| | | | |
|---|---|---|---|
| 3,614,214 | 10/1971 | Cornsweet et al. | 351/7 |
| 4,591,249 | 5/1986 | Takahashi et al. | 354/62 |
| 4,679,919 | 7/1987 | Itoh et al. | 351/206 |
| 4,756,613 | 7/1988 | Okashita | 351/206 |
| 5,270,747 | 12/1993 | Kitajima et al. | 351/205 |
| 5,365,302 | 11/1994 | Kodama | 354/403 |
| 5,371,557 | 12/1994 | Nanjho et al. | 351/206 |
| 5,371,558 | 12/1994 | Kohayakawa | 351/208 |
| 5,420,650 | 5/1995 | Kohayakawa | 351/206 |

*Primary Examiner*—Michael L. Gellner
*Assistant Examiner*—Daniel Chapik
*Attorney, Agent, or Firm*—Finnegan, Henderson, Farabow, Garrett & Dunner, L.L.P.

[57] ABSTRACT

A fundus camera capable of adjusting a working distance between a camera body and a subject's eye quickly and easily with high accuracy and capable of observing an eye fundus image in a field of view and at a magnification each substantially same as those selected when an eye fundus is photographed. To adjust the working distance quickly and easily with high accuracy, the fundus camera has an optical member 59 provided in a projecting optical system 56 for projecting alignment light onto a subject's eye E. The optical member 59 projects split alignment images onto the eye E when the working distance W is out of a predetermined proper distance. To observe the eye fundus image in the substantially same field of view and at the substantially same magnification as those selected when the eye fundus is photographed, the fundus camera has a device for, according to power variation, changing a state of illumination light illuminating the eye E. In the fundus camera, the alignment light is projected onto the eye E, the alignment light reflected by the eye E is once converged on a point R of a photographic optical path 31 conjugate with the fundus Ef of the eye E, the reflected alignment light converged thereon is guided to a TV monitor 53 through a variable power lens 53, and the state of the illumination light illuminating the eye E is changed by the changing device to observe and photograph the eye fundus Ef.

7 Claims, 13 Drawing Sheets

FUNDUS CAMERA

BACKGROUND OF THE INVENTION

1. Field of the Invention

This invention relates to a fundus camera in which alignment light is projected onto a subject's eye, the alignment light reflected by the eye is converged on a point of a photographic optical path which is conjugate with a fundus of the eye, and a camera body is adjusted with respect to the eye by receiving the reflected alignment light.

2. Description of the Prior Art

Figure 1:
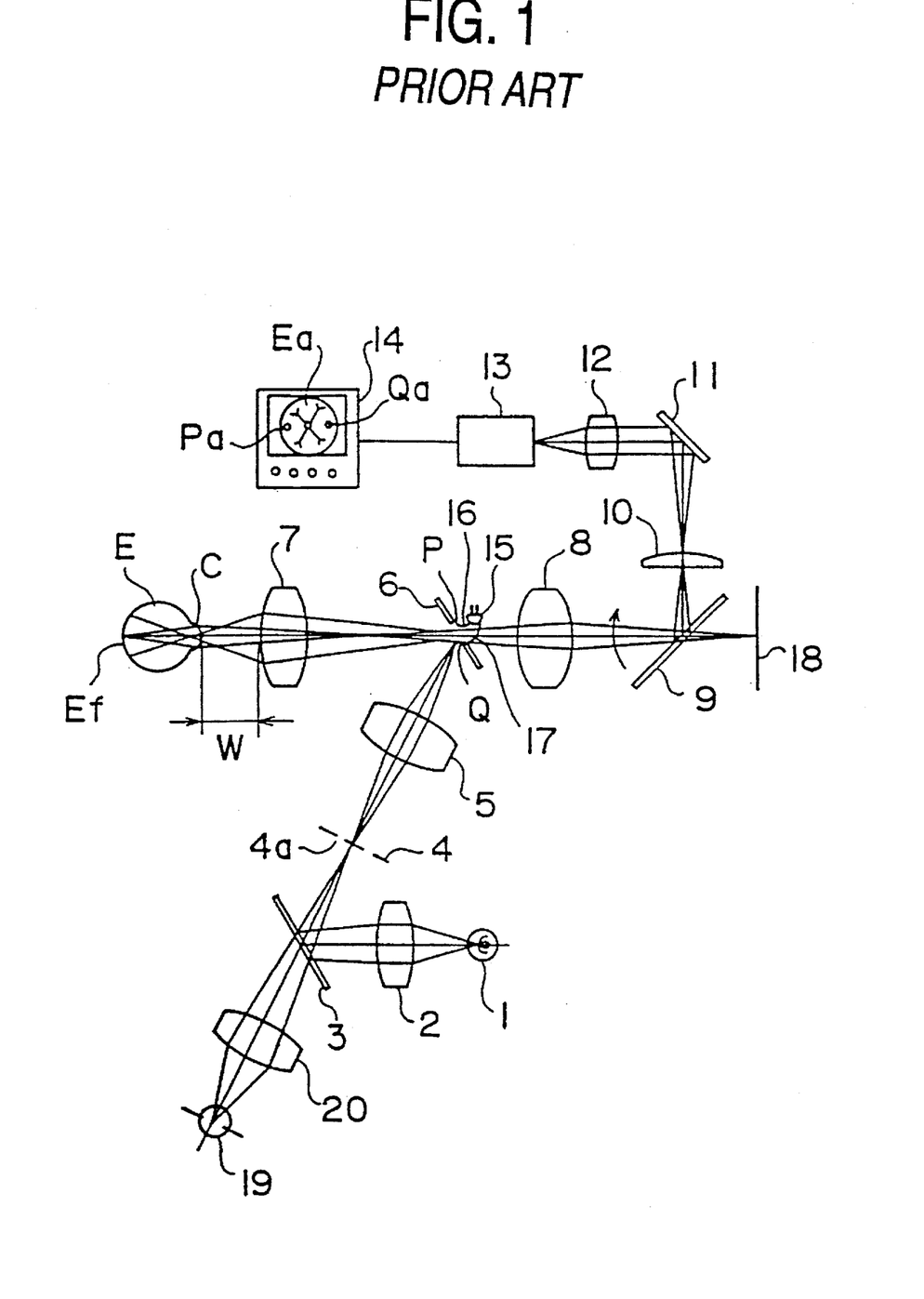
FIG. 1 is a schematic view showing an example of an optical system of a conventional fundus camera.

Conventionally, a fundus camera is known in the prior art which is shown in FIG. 1. In FIG. 1, 1 denotes an observation light source, 2 denotes a condensing lens, 3 denotes a dichroic mirror, 4 denotes a plate with a ring-shaped slit, 5 denotes a relay lens, and 6 denotes a perforated mirror. The dichroic mirror 3 has an optical characteristic in that it transmits visible light and reflects infrared light.

Illumination light emitted by the observation light source 1 is condensed by the condensing lens 2 and is reflected by the dichroic mirror 3. The light reflected by the dichroic mirror 3 is infrared light. The infrared light is guided to a ring-shaped opening 4a of the ring-shaped slit plate 4. The infrared illumination light which has passed through the ring-shaped opening 4a is guided to the perforated mirror 6 via the relay lens 5. The infrared illumination light forms an image in the vicinity of the perforated mirror 6. The infrared illumination light reflected by the perforated mirror 6 goes toward an objective lens 7 disposed in the photographic optical path. The Infrared illumination light again forms an image in the vicinity of a cornea C of the eye E, and the fundus Ef is illuminated with the infrared illumination light passing through the cornea C.

The reflected light from the fundus Ef or retina is caused to form an image as an aerial image by means of the objective lens 7 at a point conjugate with the fundus Ef. After that, the reflected light passes through an opening of the perforated mirror 6 and is guided to a field lens 10 via a photographic lens 8 and a quick return mirror 9. The reflected light is again caused to form an aerial image in the vicinity of the field lens 10. And the reflected light is received on a light-sensitive face of an image pickup tube 13, such as a CCD or a TV camera, via a reflecting mirror 11 and a relay lens 12. The image pickup tube 13 is connected to a monitor television system, and thereby an image Ea of the fundus Ef is displayed on a monitor 14.

End portions P, Q of two light guides 16, 17, such as an optical fiber, which serve to guide alignment light emitted by a light source 15 are disposed in the vicinity of the opening of the perforated mirror 6. A film 18 is disposed behind the quick return mirror 9. A shutter, not shown, is disposed between the film 18 and the quick return mirror 9. Alignment light for asking a small light spot as an alignment image on the cornea C is emitted from the end portions P, Q. The alignment light is guided to the cornea C through the objective lens 7 and is reflected by the cornea C. The reflected light from the cornea C is converged by the objective lens 7 on a point substantially conjugate with the fundus Ef and forms a small alignment image at the point. And then the reflected alignment light is guided to the image pickup tube 13 via the same optical path as the reflected light for forming the fundus image (retina image). Thereby, two alignment images are formed on the image pickup tube 13. Accordingly, two small light spots Pa, Qa which are each an alignment image are displayed on a screen of the TV monitor 14.

A photographer (operator) observes the retina image Ea displayed on the screen of the TV monitor 14 while focusing the image Ea to select a portion of the fundus to be photographed. Further, the photographer judges whether the light spots Pa, Qa are in focus and are normally positioned. According to the judgment, the correlative locations of the camera body and the subject's eye are determined. In the conventional fundus camera, a photographic light source 19 and a condenser lens 20 are disposed behind the dichroic mirror 3. When a photograph is taken, the photographic light source 19 is caused to emit light. The photographic light emitted by the photographic light source 19 passes through the condenser lens 20 and the dichroic mirror 3 and illuminates the eye fundus Ef with the visible illumination light. The light reflected by the eye fundus Ef forms an image on the film 18.

Conventionally, a fundus camera is also known in which the eye fundus is photographed in variable power. Such power variation is useful to examine the eye. However, the variation of a photographic lens from low power to high power during the observation of the eye fundus causes a field of view for observation (a field of view for photography) to be narrowed. For this reason, the light spots Pa and Qa are placed out of the field of view and therefore the positions of the camera body and the eye E cannot be determined.

Figure 2:
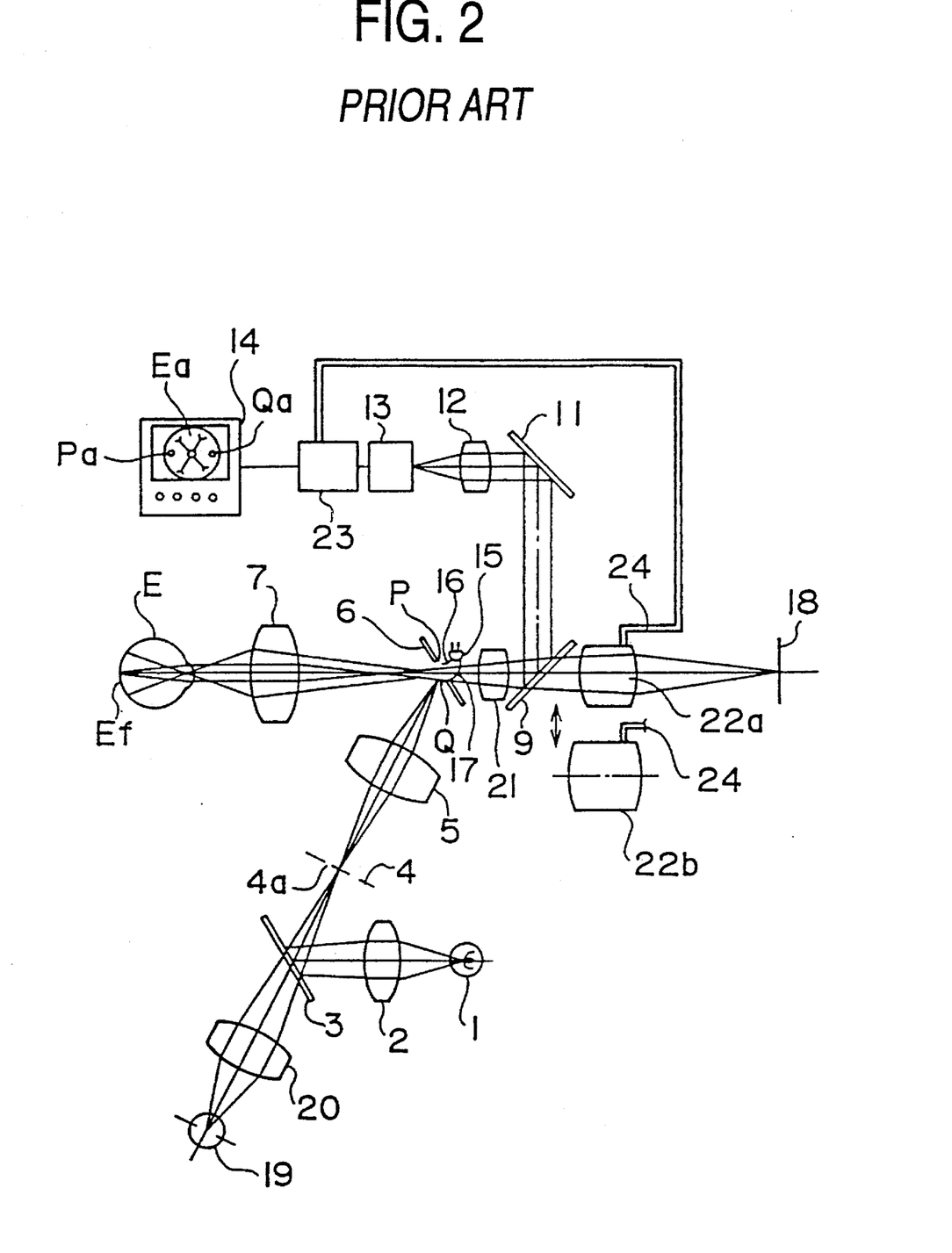
FIG. 2 is a schematic view showing another example of the optical system of the conventional fundus camera.

To resolve this problem, an optical system of a fundus camera shown in FIG. 2 is known. In this optical system, a focussing lens 21 is disposed between the perforated mirror 6 and the quick return mirror 9. Further, photographic lenses 22a, 22b, each variable power lenses are interchangeably disposed in a photographic optical path behind the quick return mirror 9. Therefore, according to this conventional fundus camera, the light spots Pa and Qa are prevented from being placed out of the field of view since the alignment light is relayed to the image pickup tube 13 before the photographic lenses 22a and 22b. Further, a character synthesizing device 23 is disposed between the image pickup tube 13 and the monitor TV 14. Further, an electric contact 24 is attached to each of the photographic lenses 22a, 22b. The electric contact 24 serves to input information about the powers of the photographic lenses 22a, 22b in use to the character synthesizing device 23.

Figure 3A:
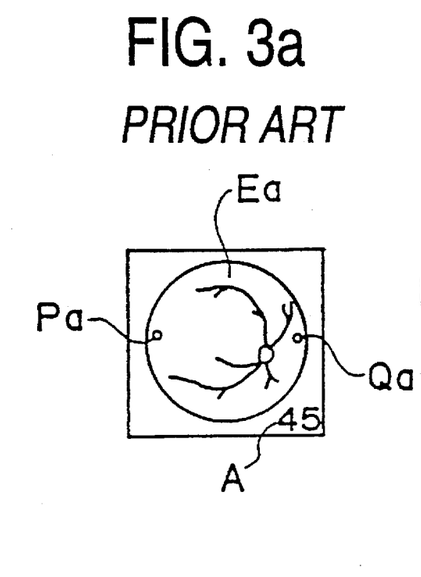
Figure 3B:
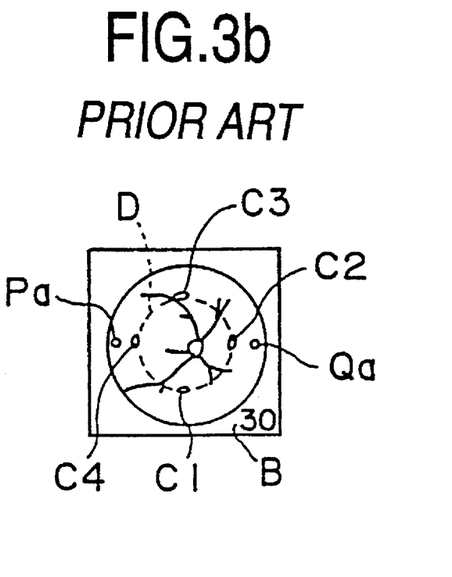
Figure 4:
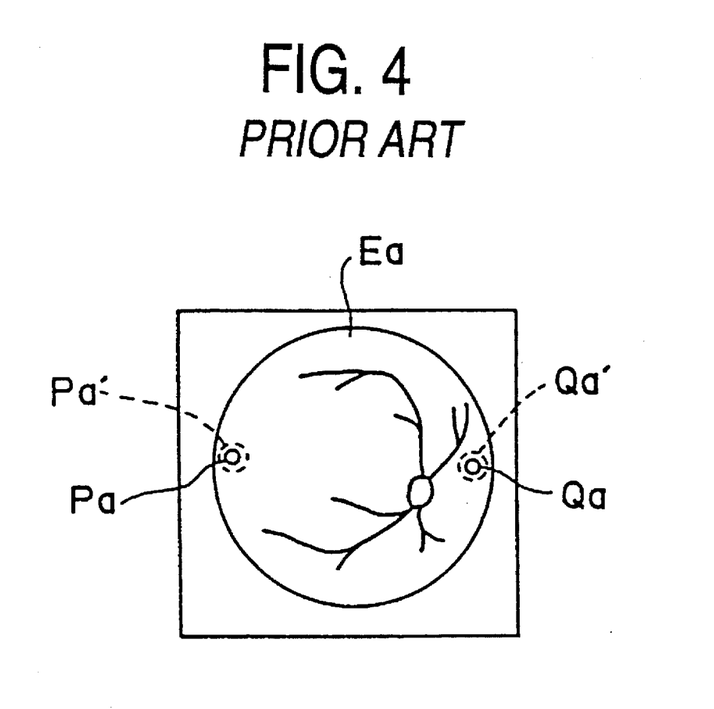
FIG. 4 is a view for describing a disadvantage of the conventional fundus camera.

Let it be supposed that the photographic lens 22a is inserted in the photographic optical system and a photographic angle of view A (45°) is displayed as shown in (a) of FIG. 3. When the photographic lens 22a is removed from the photographic optical path and the photographic lens 22b is inserted thereinto instead, the photographic power is varied from high to low. Accordingly, the picture displayed on the monitor TV 14 is changed from (a) of FIG. 3 to (b) of FIG. 3. That is, the character synthesizing device 23 causes not only a ring D representing a photographic field of view but also a numeral representing a photographic angle of view B (30°) to be displayed on the monitor TV 14. In (b) of FIG. 3, C1 through C4 each designate a target. However, according to this conventional fundus camera, when a working distance W (see FIG. 1) between the eye and the camera body is improper, the light spots Pa, Qa which are alignment images grow faint and low in brightness as shown by Pa', Qa' of FIG. 4 as an enlarged view. Accordingly, the working distance W is adjusted so that the light spots Pa, Qa grow clear. However, according to the conventional fundus camera, if the working distance W is improper even slightly, the light spots Pa, Qa abruptly grow faint. Therefore, the working distance W cannot be easily adjusted. Further, alignment accuracy still depends on operator's skill.

Further, according to the fundus camera shown in FIG. 2 in which the magnification of an eye fundus image is varied, since its magnification in observation is different from that in photography, the photographer will have a sense of inconvenience. Further, since the variation in magnification of an eye fundus image from low to high inevitably leads to the variation in magnification of an alignment image, the alignment image grows low in brightness, hence it becomes difficult to clearly observe the alignment image.

SUMMARY OF THE INVENTION

It is a first object of the invention to provide a fundus camera in which quick and easy adjustment to a working distance can be made with high accuracy.

It is a second object of the invention to provide a fundus camera in which an eye fundus image can be observed in a field of view and at a magnification each substantially same as those selected when an eye fundus is photographed and therefore a judgment whether in alignment or not is correctly formed.

To accomplish the first object, the fundus camera according to the invention includes an optical member which is included in a projecting means for projecting alignment light onto a subject's eye. In the fundus camera arranged such that the alignment light reflected by the eye is once converged on a point of a photographic path conjugate with the fundus of the eye and is received to observe and photograph the fundus, the optical member projects split alignment images made of the alignment light onto the eye when the working distance between a camera body and the eye is out of a predetermined proper condition. According to the fundus camera, since the split alignment images are projected onto the eye when the working distance therebetween is out of the predetermined proper condition, quick and easy adjustment to the working distance can be made with high accuracy.

To accomplish the second object, the fundus camera according to the invention includes a scans for changing a state of illuminating the eye with alignment light according to the power variation of a variable power lens. The fundus camera having the changing means is characterized in that the alignment light projected onto the eye and reflected thereby is once converged on a point of a photographic path conjugate with the fundus of the eye and is received via the variable power lens to observe and photograph the fundus. According to this fundus camera, since the reflected alignment light is received via the variable power lens and, according to the power variation of the variable power lens, the changing means changes the illumination state, an eye fundus image can be observed in a field of view and at a magnification each substantially same as those selected when the eye fundus is photographed and therefore a judgment whether in alignment or not is correctly formed. Further, since an eye fundus image formed according to the power variation of the variable power lens is observed, the operator can remove the sense of inconvenience.

BRIEF DESCRIPTION OF THE DRAWINGS

FIG. 3 shows eye fundus images displayed on a TV monitor shown in FIG. 2, wherein (a) is an eye fundus image taken at low magnification and (b) is an eye fundus image taken at high magnification.

FIG. 8 shows light spots formed by reflected alignment light, wherein (a) shows a case in which a working distance between the fundus camera and the eye is proper and (b) shows a case in which the working distance is improper.

FIG. 12 shows eye fundus images displayed on a TV monitor shown in FIG. 11, wherein (a) is an eye fundus image taken at low magnification and (b) is an eye fundus image taken at high magnification.

FIG. 14 shows a fifth embodiment of the fundus camera according to the invention, wherein (a) is an eye fundus image taken at low magnification and (b) is an eye fundus image taken at high magnification.

FIG. 18 is another variant of the fundus camera according to the invention, wherein (a) is an eye fundus image taken at low magnification and (b) is an eye fundus image taken at high magnification.

DETAILED DESCRIPTION OF THE PREFERRED EMBODIMENTS

First Embodiment

Figure 5:
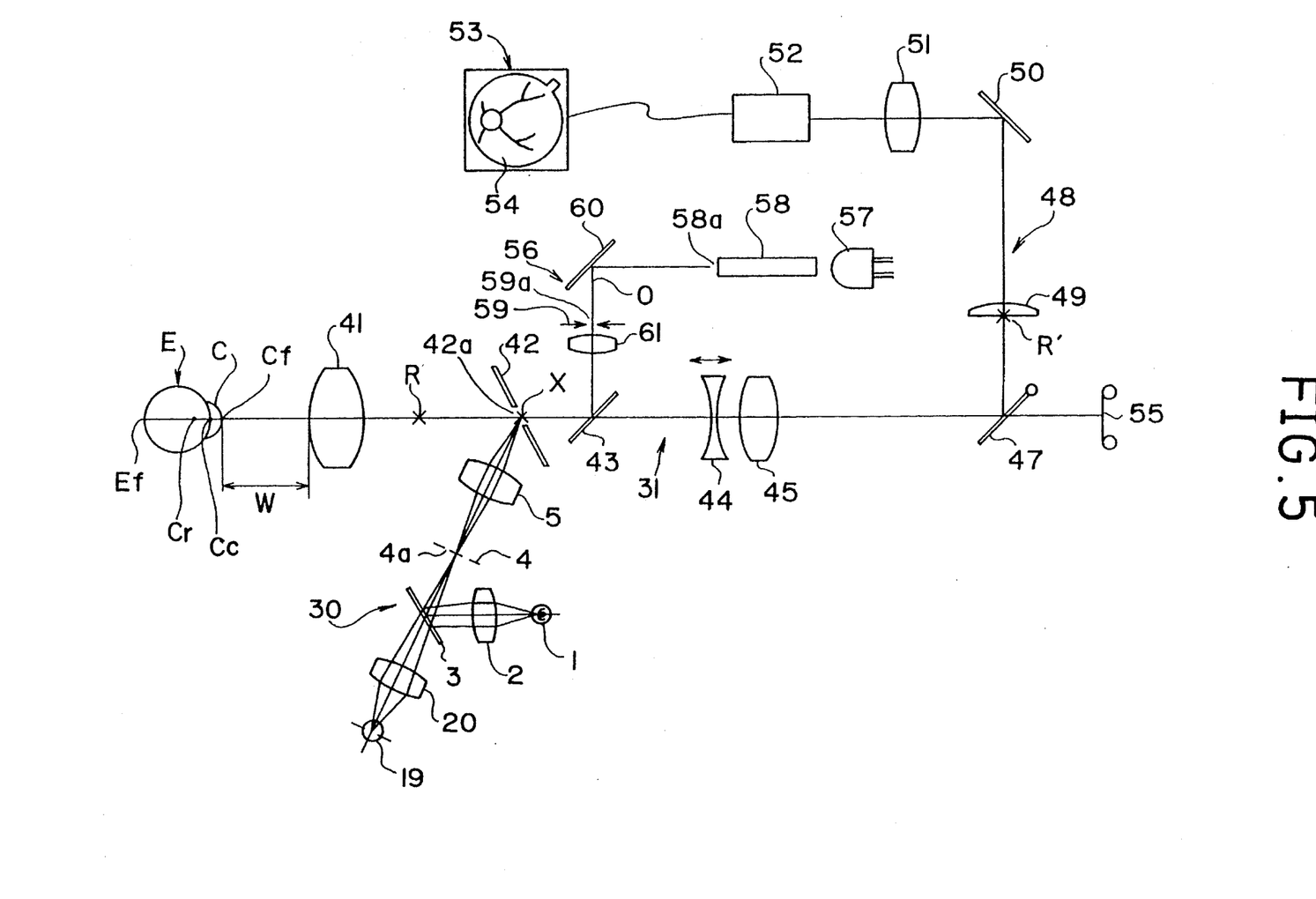
FIG. 5 is a schematic view showing a first embodiment of a fundus camera according to the invention.

Referring to FIG. 5, 30 designates an illumination optical system and 31 designates a photographic optical system. Since the makeup of the illumination optical system 30 of the invention is the same as that of a conventional fundus camera shown in FIG. 1, the same numerals as those shown in FIG. 1 are given to the corresponding elements of the invention and a detailed description of each element will be omitted.

The photographic optical system 31 includes an objective lens 41, a perforated mirror 42, a half mirror 43, a focusing lens 44, an image formation lens 45, and a quick return mirror 47. Light reflected by an eye fundus Ef is guided to the objective lens 41 and is once caused to form an image at a point R conjugate with the eye fundus Ef by the objective lens 41. After that, the reflected light passes through a hole 42a of the perforated mirror 42 and the half mirror 43 and is guided to the quick return mirror 47 via the focusing lens 44 and the image formation lens 45. By the quick return mirror 47, the reflected light is again caused to form an image at a point R' where a field lens 49 as a component of an observation optical system 48 is disposed. And the reflected light is received by an image pickup tube 52 via a reflecting mirror 50 and a TV relay lens 51. The image pickup tube 52 is electrically connected to a TV monitor 58 as a displaying means. By an output from the image pickup tube 52, an eye fundus image 54 is displayed on a screen of the TV monitor 53.

In the photographic optical system 31, a film 55 is disposed at a point conjugate with the field lens 49 with respect to the quick return mirror 47. In photography, the quick return mirror 47 is removed from an optical path of the photographic optical system 31 at the same time as light is emitted from the photographic light source 19. Thereby, the reflected light from the eye fundus Ef is caused to form an image of the eye fundus Ef on the film 55.

Figure 7:
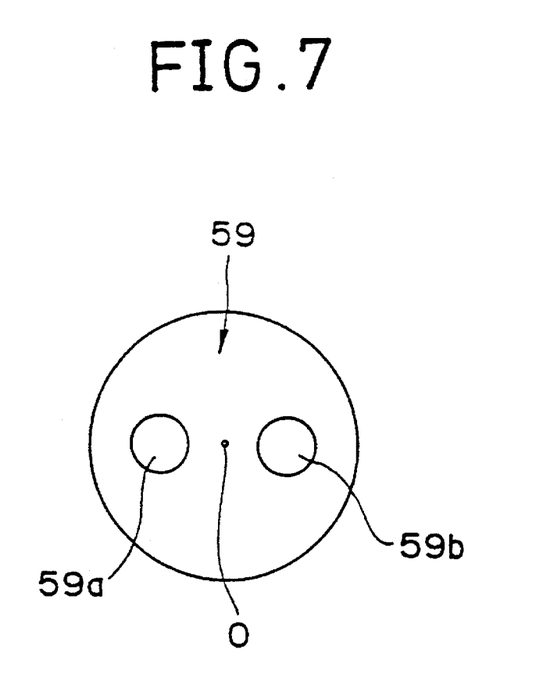
FIG. 7 is a plan view showing a two-hole diaphragm shown in FIG. 5.

The half mirror 43 is a part of a projecting means 56 for projecting alignment light onto the eye. The projecting means 56 includes an LED 57 as an alignment light source, a light guide 58, a reflecting mirror 60, and a relay lens 61. The LED 57 emits near infrared light having a central wavelength of 760 nm. An emission edge 58a of the light guide 58 is arranged so as to be located in an optical axis O of the relay lens 61. A two-hole diaphragm 59 as an optical member is disposed between the relay lens 61 and the reflecting mirror 60. As shown in FIG. 7, the two-hole diaphragm 59 has a pair of holes or transparent portions 59a, 59b. The holes or transparent portions 59a, 59b are symmetrical with respect to the optical axis O. The two-hole diaphragm 59 is disposed next to the relay lens 61.

Figure 6:
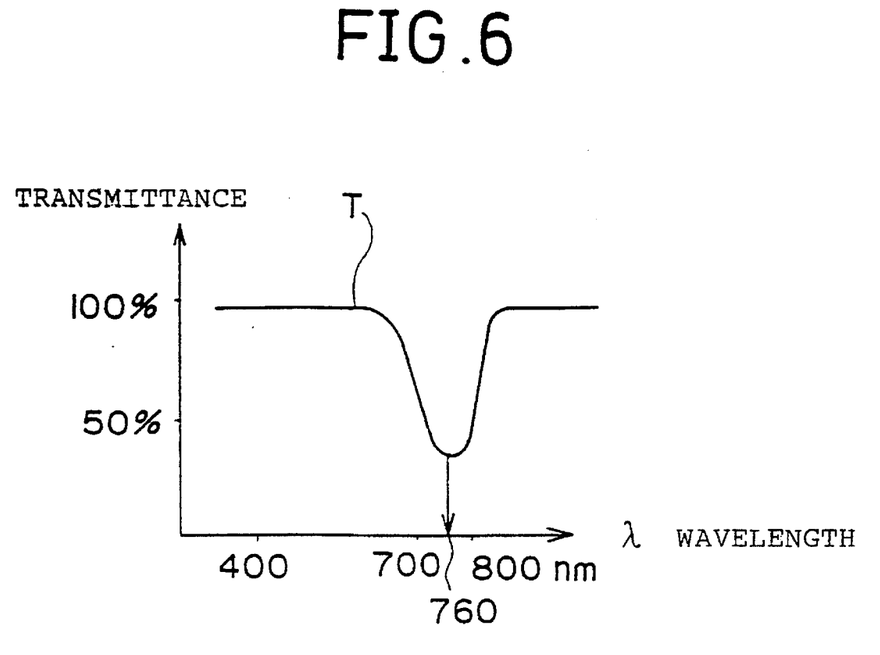
FIG. 6 is a graph showing a transmittance characteristic of a half mirror shown in FIG. 5.

The alignment light emitted from the emission edge 58a is reflected by the reflecting mirror 60 and is guided to the holes or transparent portions 59a, 59b. The alignment light which has passed through the holes or transparent portions 59a, 59b is guided to the relay lens 61. The alignment light which has passed through the relay lens 61 is reflected by the half mirror 43 toward the perforated mirror 42. The relay lens 61 forms an image of the emission edge 58a at the center X of the hole 42a of the perforated mirror 42. As shown in FIG. 6, a transmittance characteristic T of the half mirror 43 is that the half mirror 43 transmits nearly half the alignment light having a wavelength of 760 nm and transmits nearly all the alignment light having wavelengths other than that of 760 nm.

Owing to the disposition of the half mirror 43, the amount of the reflected light from the eye fundus Ef is prevented from being lessened.

A pair of beams of the alignment light which have formed an image at the center X of the hole 42a are guided to a cornea C of the eye E via the objective lens 41. If the working distance W between the camera body and the eye E and the positions in the up, down, right, and left directions are each in a proper condition when the alignment light beams are guided thereto, an alignment image is formed, according to the alignment light beams which have passed through the holes or transparent portions 59a, 59b, at a point Cc corresponding to ½ of the center of curvature of the cornea C. The point Cc resides in the middle between the apex Cf of the cornea C and the corneal center of curvature Cr.

If the working distance W is out of the predetermined proper condition, the alignment image formed according to the pair of beams of the alignment light is split relative to the point Cc which is ½ of the corneal center of curvature Cr. In other words, the two-hole diaphragm 59 serves as an optical member for splitting an alignment image according to the alignment light and projecting split images onto the eye E when the working distance W is out of the predetermined condition.

As for the alignment image (i.e., image of the emission edge 58a) formed at the cornea C according to the alignment light, since the two-hole diaphragm 59 is disposed immediately before the relay lens 61, the depth of focus of the relay lens 61 is deepened. Therefore, even if the working distance W is slightly out of the proper condition, unclearness or unsharpness of the image can be reduced.

Figure 8A:
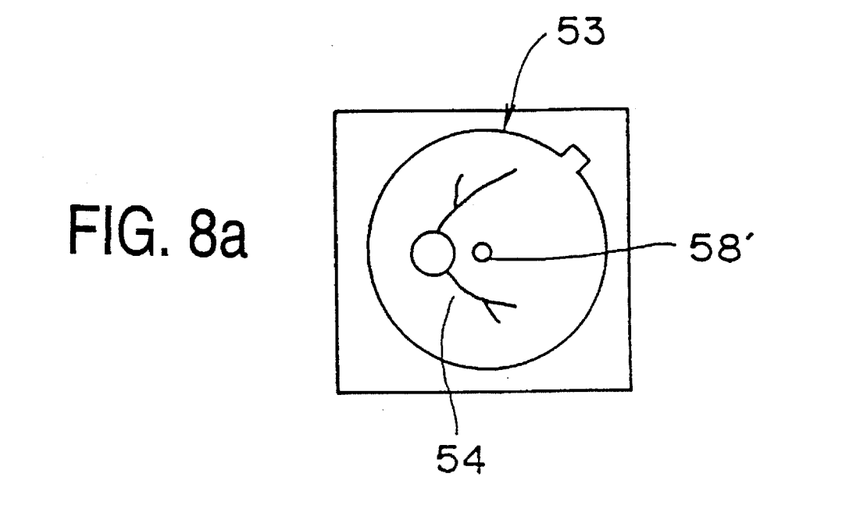
Figure 8B:
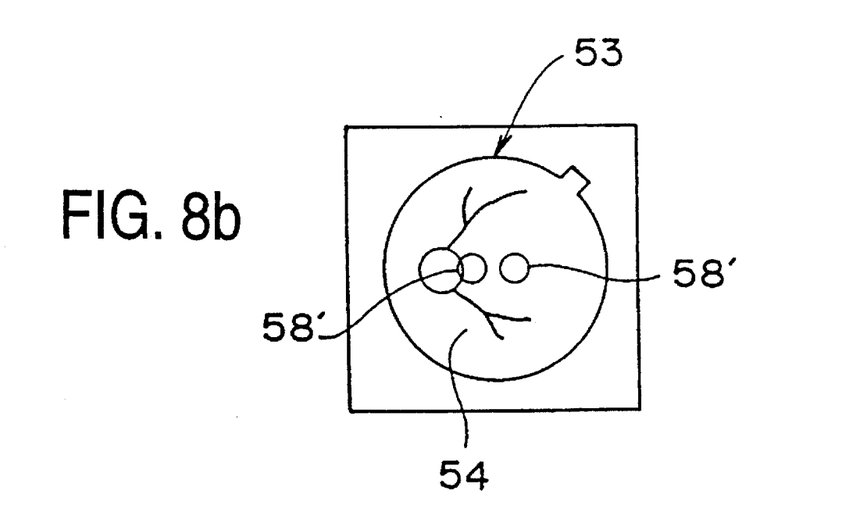

When the working distance W is in the proper condition, the reflected alignment light from the cornea C forms an image at the conjugate point R with the eye fundus Ef by means of the objective lens 41. The reflected alignment light converged on the point R passes through the hole 42a and is received on the image pickup tube 52 in the same way as the reflected light for forming an eye fundus image is done. And, as shown in (a) of FIG. 8, a light spot 58' as an alignment image (image of the emission edge 58a) as well as an eye fundus image 54 is displayed on the screen of the TV monitor 53. On the other hand, when the working distance W is out of the proper condition, the light spot 58' is split as shown in (b) of FIG. 8. Therefore, the operator can perform the alignment adjustment by observing the light spot 58' which is displayed as a single image or split images on the screen of the TV monitor 53.

Second Embodiment

Figure 9:
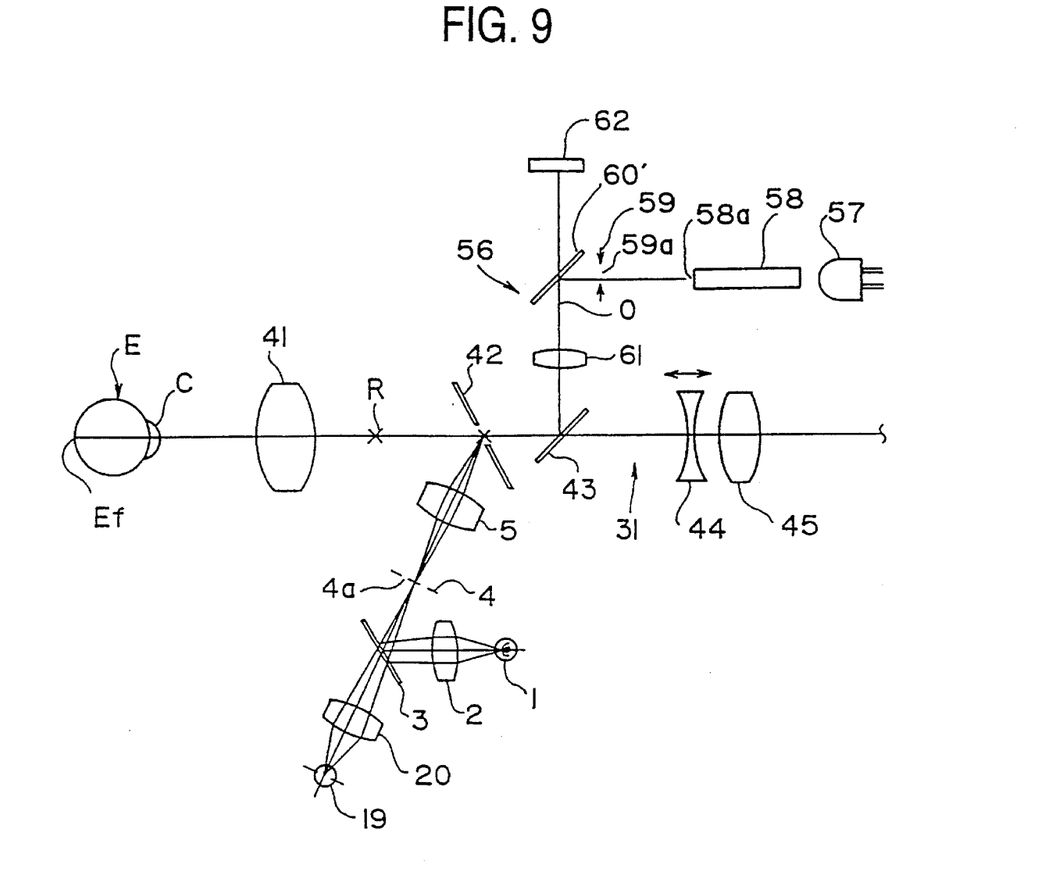
FIG. 9 is a schematic view of main portions of an optical system showing a second embodiment of the fundus camera according to the invention.
Figure 10:
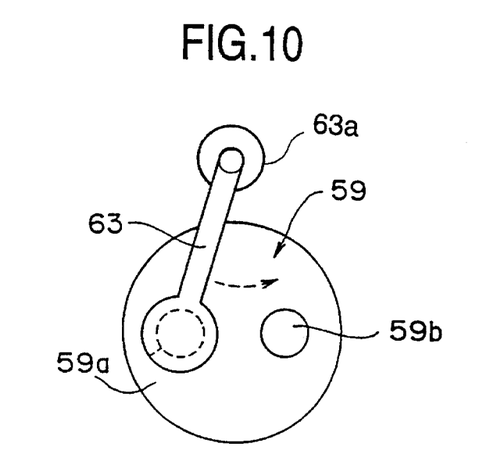
FIG. 10 is a variant of the second embodiment shown in FIG. 9.

FIG. 9 shows a second embodiment of the fundus camera according to the invention. In the second embodiment, a half mirror 60' is disposed instead of the reflecting mirror 60 and further a position sensor 62 for receiving the alignment light reflected by the half mirror 43 is disposed behind the half mirror 60'. The position sensor 62 is conjugate with the point R with respect to the relay lens 61. If the working distance between the eye E and the camera body is in the predetermined condition and the position of the camera body relative to the eye E in the up, down, right, and left directions is also in the predetermined condition, a photographic signal is automatically output to a circuit (not shown) for controlling the light emission of a xenon tube. The two-hole diaphragm 59 is disposed between the half mirror 60' and the light guide 58 and near the half mirror 60'. Accordingly, an eye fundus image 54 is automatically taken. In this connection, the optical system can be arranged so as to stop photographing the eye fundus when either the working distance W or the position of the camera body relative to the eye E is out of the predetermined condition. Also, in the first embodiment, an arrangement can be adopted in which automatic photography is performed according to an output signal of the image pickup tube (TV camera) 52. FIG. 10 shows the two-hole diaphragm 59 according to the invention, in which the holes or transparent portions 59a, 59b are alternately stopped up with a light intercepting member 63 by a drive member 63a such as, for example, a well-known rotary solenoid. The light intercepting member 63 swings back and forth at the urging of the drive member 63a, as shown by the dotted line arrow in FIG. 10. By thus constructing the two-hole diaphragm 59, an alignment image projected onto the cornea C according to the reflected alignment light flickers when the working distance W is out of the proper condition. When the working distance W is in the proper condition, the projected alignment image is kept bright. Accordingly, the operator can quickly judge whether or not the working distance W is in the proper condition.

Third Embodiment

Figure 11:
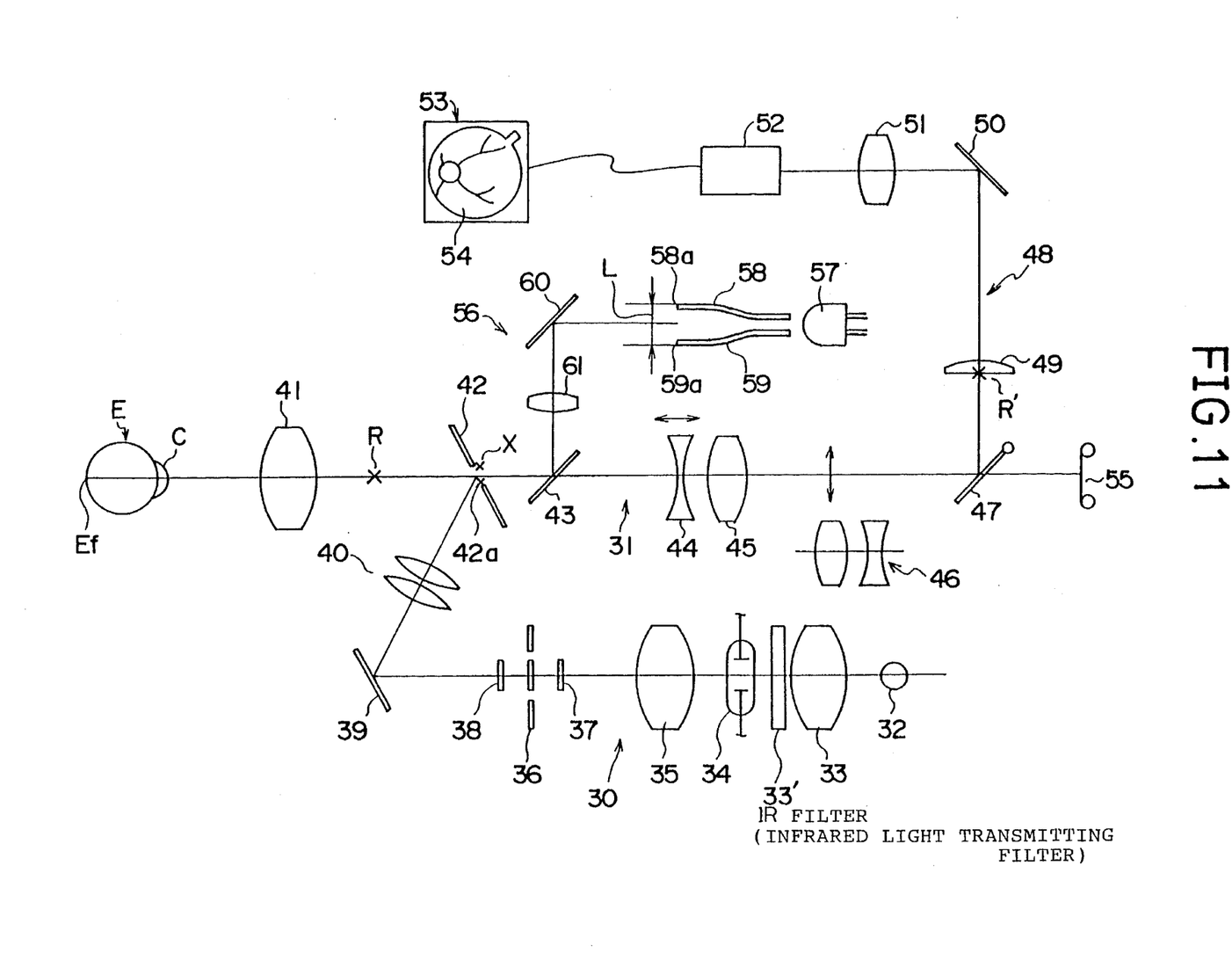
FIG. 11 is a schematic view showing a third embodiment of the fundus camera according to the invention.

FIG. 11 shows a third embodiment of the fundus camera according to the invention.

The illumination optical system 30 includes an observation light source 32 such as a tungsten lamp, a condenser lens 33, an IR filter (infrared filter) 33', a photographic light source 34 such as a xenon tube, a condenser lens 35, a ring-slit plate 36, black-spot plates 37 and 38, a reflecting mirror 39, and a relay lens 40. The photographic optical system 31 includes a variable power lens 46 between the image formation lens 45 and the quick return mirror 47.

In the third embodiment, the observation light source 32 emits light all the time, whereas the photographic light source 34 emits light only when photographed. Illumination light emitted by the observation light source 32 is converged on the position of the photographic light source 34 by the condenser lens 33 and is guided to the condenser lens 35 as if the light is emitted from the photographic light source 34. The illumination light is condensed by the condenser lens 35 and is guided to the eye E to illuminate the eye fundus Ef via the black-spot plate 37, ring-slit plate 36, black spot plate 38, reflecting mirror 39, and relay lens 40, as in the first embodiment. Light reflected by the eye fundus Ef passes through the photographic optical path as in the first embodiment and is received by the image pickup tube 52 to form an eye fundus image as in the first embodiment. And the eye fundus image is displayed on the screen of the TV monitor 53.

In the third embodiment, the projecting means 56 includes the LED 57 as an alignment light source, light guides 58 and 59, reflecting mirror 60, and relay lens 61. As in the first embodiment, a central wavelength of the LED 57 is 760 nm. Alignment light emitted from each of emission edges 58a and 59a of the light guides 58 and 59 is reflected by the reflecting mirror 60 and is guided to the relay lens 61. The alignment light which has passed through the relay lens 61 is reflected by the half mirror 43 and is once converged on a point X positioned on the periphery of the hole 42a of the perforated mirror 42 (i.e., a point X out of the optical axis of the photographic optical path). Images of the emission edges 58a and 58b are once formed at the point X. The half mirror 43 has the same transmittance characteristic W as that in the first embodiment (see FIG. 6).

Figure 12A:
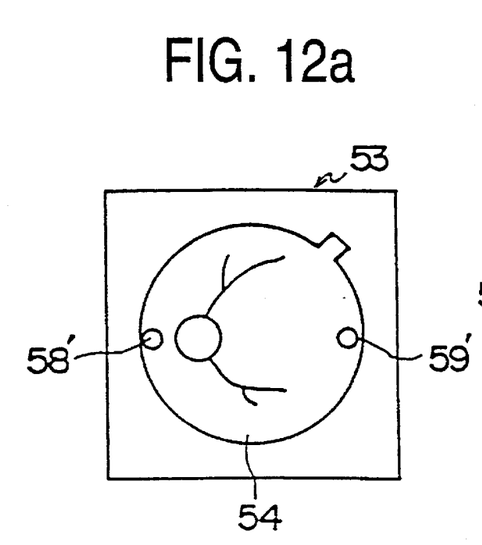
Figure 12B:
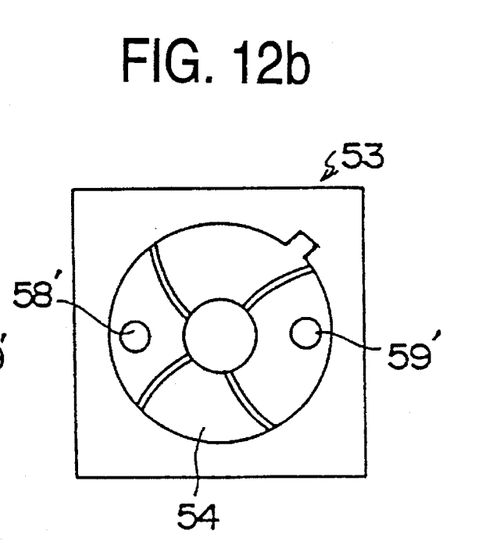

The variable power lens 46 is removed from the optical path of the photographic optical system 31 when the power of the lens 46 is low. The alignment light reflected by the cornea C is caused to form an image by means of the objective lens 41 at a point R conjugate with the eye fundus Ef. The reflected alignment light converged on the point R passes through the hole 42a and is received by the image pickup tube 52 in the same way as the reflected light for forming an eye fundus image is done. As shown in (a) of FIG. 12, light spots 58' and 59' corresponding to the emission edges 58a and 59a are displayed on the screen of the TV monitor 53 together with an eye fundus image 54. Emission edge portions of the light guides 58 and 59 are held by a movable clamp member (not shown). Thereby, a distance L between the emission edges 58a and 59a is adjustable. When the variable power lens 46 is inserted into the optical path of the photographic optical system 31, the eye fundus image is varied and enlarged as shown in (b) of FIG. 12. Simultaneously with the insertion of the variable power lens 46 into the photographic optical system 31, the movable clamp member displaces the emission edge portions of the light guides 58 and 59 so that the distance L is shortened.

Thereby, a state of the alignment light illuminating the eye E is changed. Therefore, the light spots 58' and 59' each enlarged according to a photographic magnification are displayed on the screen of the TV monitor 53. In order to keep the brightness of the light spots 58' and 59' received by the image pickup tube 52 constant, the amount of emission light of the LED 57 can be increased or decreased in connection with the insertion or removal of the variable power lens 46 into or from the photographic optical path.

Fourth Embodiment

Figure 13:
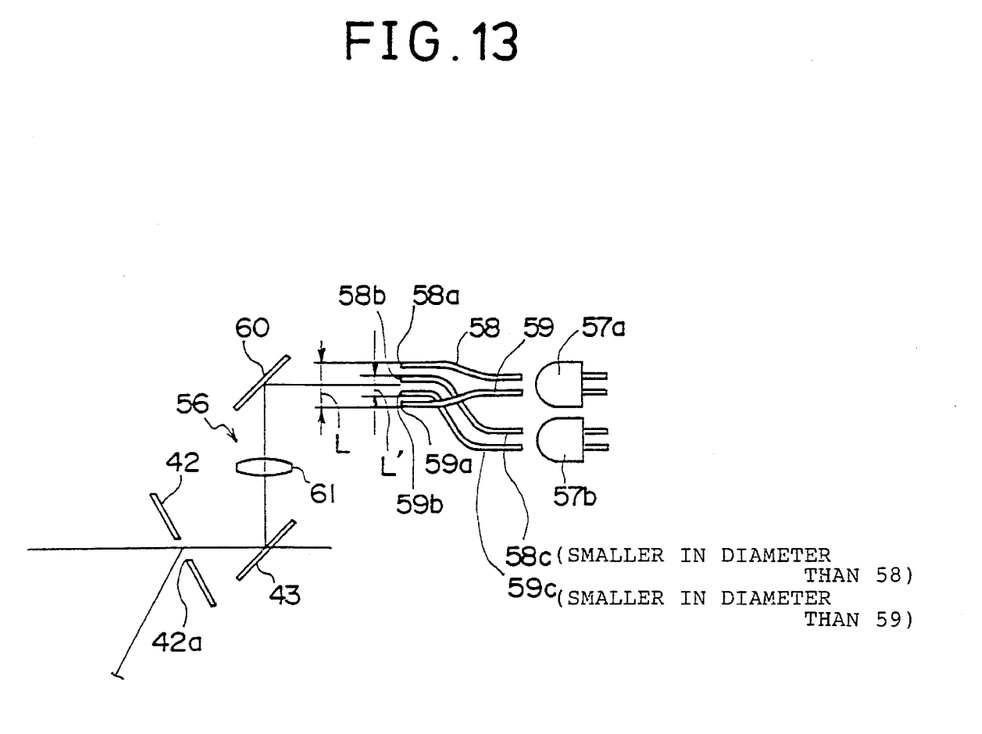
FIG. 13 is a schematic view of a main portion of an optical system showing a fourth embodiment of the fundus camera according to the invention.

FIG. 13 is a schematic view of a main portion of an optical system showing a fourth embodiment of the fundus camera according to the invention. In the fourth embodiment, two LEDs 57a and 57b are used as an alignment light source. Further, light guides 58, 59, 58c, and 59c are used. A distance L between the emission edges 58a and 59a of the light guides 58 and 59 is made large, whereas s distance L' between the emission edges 58b and 59b of the light guides 58c and 59c is made relatively small. In the case of low power, alignment light is emitted from the LED 57a. Accordingly, the alignment light is projected from the emission edges 58a and 59a to the cornea C of the eye E. On the other hand, in the case of high power, alignment light is emitted from the LED 57b, and accordingly, is projected from the emission edges 58b and 59b to the cornea C of the eye E. According to the fourth embodiment, a state of the alignment light illuminating the eye E can be changed without such a movable clamp member as in the third embodiment. In the fourth embodiment, in order to keep the brightness and size of the light spots 58' and 59' received by the image pickup tube 52 constant, the amount of light of the LED and the thickness of the light guides can be predetermined, respectively.

Figure 14A:
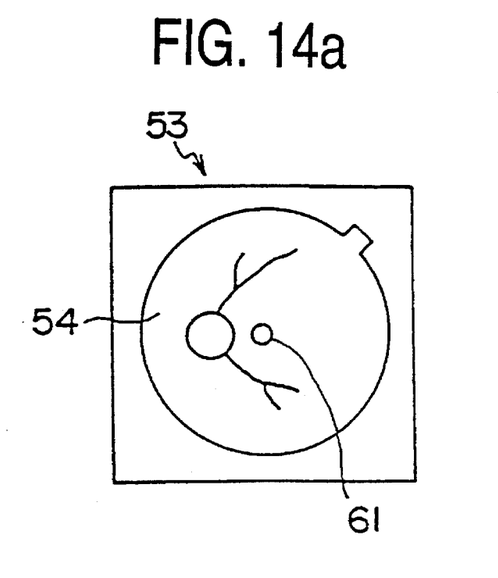
Figure 14B:
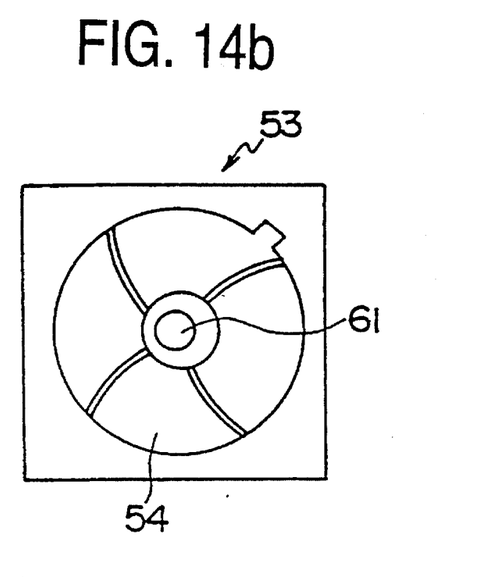

Fifth Embodiment (a) and (b) of FIG. 14 are diagrams for describing a fifth embodiment of the fundus camera according to the invention.

In this embodiment, an arrangement is adopted in which the emission edge of a single light guide is disposed on the optical axis of the projecting means 56 and a single alignment image is projected to the apex of the cornea C. In this case, a single light spot 61 is displayed on the screen of the TV monitor 53. (a) of FIG. 14 shows a case of low power and (b) of FIG. 14 shows a case of high power, in the case of the high power, the light spot 61 itself together with the eye fundus image 54 is magnified in size and is lessened in brightness. Therefore, with the variation of the power from low to high, the amount of the alignment light emitted from the LED 57 is increased, hence a state of the alignment light illuminating the eye E is changed. According to the fifth embodiment, the brightness of the light spot 61 on a plane conjugate with the eye fundus Ef can be made constant.

The preferred embodiments have been described as above. Reference will be again made to the third and fifth embodiments. In the third and fifth embodiments, if the diameters of the emission edges 58a and 59a are shortened according to the variation of the eye fundus image from low power to high power, the sizes of the light spots 58' and 59' can be made constant regardless of the power variation.

Figure 15:
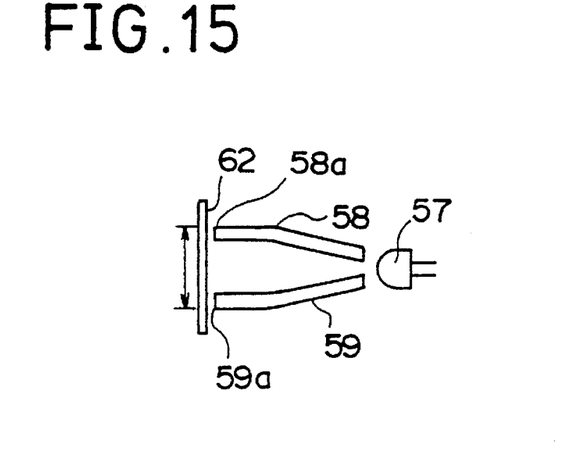
FIG. 15 is a detailed view of a main portion of an optical system showing a variant of the third embodiment of the fundus camera according to the invention.
Figure 16:
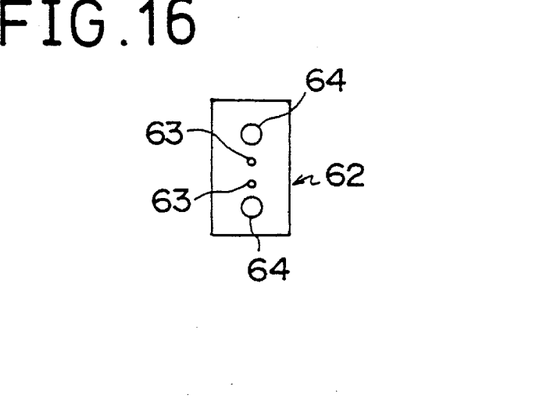
FIG. 16 is a front elevation of a diaphragm plate shown in FIG. 15.

That is, as shown in FIG. 15, a diaphragm plate 62 is disposed in the vicinity of the emission edges 58a and 59a of the light guides 58 and 59 of the third embodiment. Further, as shown in FIG. 16, diaphragm holes 63 and 63 for high power and diaphragm holes 64 and 64 for low power are formed in the diaphragm plate 62. And a distance L between the emission edges 58a and 59a is adjusted with respect to the diaphragm plate 62. Accordingly, the sizes of the light spots 58' and 59' can be varied.

Figure 17:
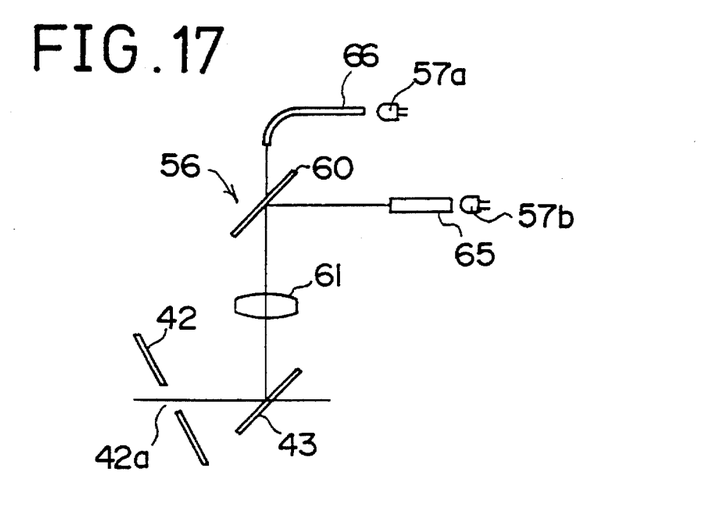
FIG. 17 is a schematic view of main portions of an optical system showing a variant of the fifth embodiment of the fundus camera according to the invention.

Further, as shown in FIG. 17, a half mirror is used as the reflecting mirror 60 disposed in the optical path of the projecting means, a large light guide in diameter is used as the light guide 65 for low power, and a small light guide in diameter is used as the light guide 66 for high power. Accordingly, the sizes of the light spots 58' and 59' can be also varied.

Figure 18A:
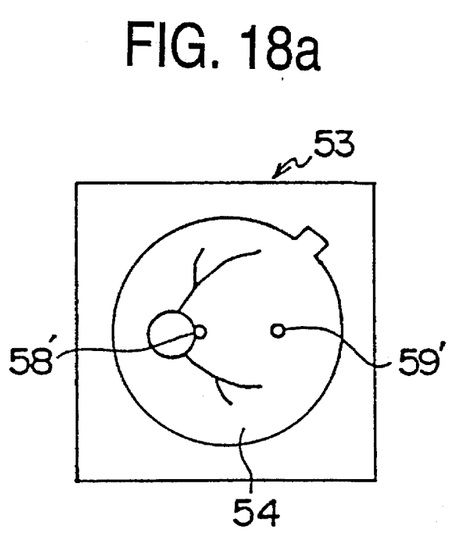
Figure 18B:
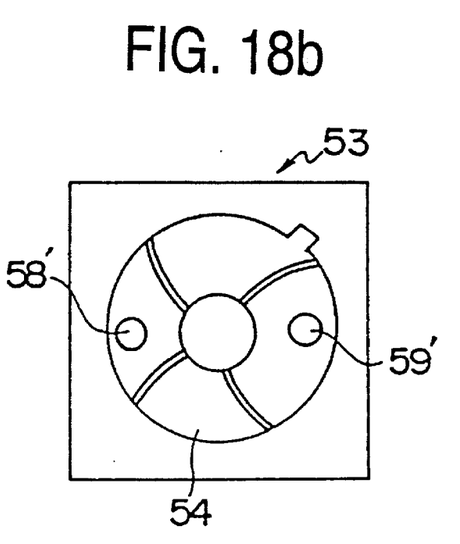

Further, if the distance L between the emission edges 58a and 59a shown in FIG. 11 is set such that the light spots 58' and 59' are displayed near the side lines of the screen of the TV monitor 53 in the case of high power as shown in (b) of FIG. 18 whereas they are displayed near the center of the screen in the case of low power as shown in (a) of FIG. 18, the light spots 58' and 59' can be displayed according to the power variation without changing the state of the alignment light illuminating the eye E.

What is claimed is:

1. A fundus camera comprising:

an illumination optical system for illuminating a fundus of a subject's eye with illumination light;

projecting means for projecting two beams of alignment light onto a cornea of the eye in order to align a camera body with the eye, the beams coinciding to form a single alignment image on the eye when a working distance between a camera body and the eye is in a predetermined proper condition, the beams forming two split alignment images on the eye when the working distance between the camera body and the eye is out of the predetermined proper condition;

a photographic optical system having an objective lens disposed in front of the eye, the illumination light being reflected by the fundus of the eye and converged upon a point conjugate with the fundus by the objective lens so as to form a fundus image as an aerial image and then be guided to an image pickup tube, the alignment light being projected onto the cornea and converged upon the point conjugate with the fundus so as to form an alignment image as an aerial image and be guided to said image pick tube; and display means for displaying the fundus image and the alignment image each formed on said image pickup tube.

2. A fundus camera according to claim 1, wherein said photographic optical system further includes a perforated mirror defining a hole therethrough, said perforated mirror serving to reflect the illumination light toward said objective lens and permit the reflected light from the fundus to pass through the hole toward said image pickup tube, and an image formation lens for converging the reflected light upon said image pickup tube to form an image, said projecting means including an alignment light source, a relay lens for causing alignment light emitted by said alignment light source to form an image in the middle of the hole of said perforated mirror, and a diaphragm having a pair of light transmitting portions and being disposed between said relay lens and said alignment light source for splitting the alignment light emitted by said light source into the two beams and guiding the two beams to said relay lens.

3. A fundus camera according to claim 1, wherein the projecting means further includes a light intercepting member swingably mounted for alternately blocking the beams causing the two split alignment images to flicker when the working distance is out of the predetermined proper condition.

4. A fundus camera according to claim 1, wherein said photographic optical system further includes a position sensor for, based on the alignment image, detecting the working distance between the camera body and the eye and according to which a circuit for controlling light emission of a xenon tube is driven and directing the photographic optical system to take a photograph when the working distance is in the predetermined proper condition.

5. A fundus camera comprising:

an illumination optical system for illuminating a fundus of a subject's eye with illumination light;

projecting means for projecting alignment light onto a cornea of the eye in order to align a camera body with the eye;

a photographic optical system having an objective lens disposed in front of the eye, the illumination light being reflected off the fundus of the eye and converged upon a point conjugate with the fundus by the objective lens so as to form a fundus image as an aerial image at the conjugate point and be guided to an image pickup tube, the alignment light being projected onto the cornea and converged upon the point conjugate with the fundus so as to form an alignment image as an aerial image at the conjugate point and be guided to the image pickup tube, said photographic optical system including a perforated mirror with a hole, an image formation lens for causing the reflected illumination light from the fundus to form an image, and a variable power lens, said perforated mirror reflecting the illumination light toward said objective lens and permitting the reflected light from the fundus to pass through the hole toward said image pickup tube, said variable power lens being disposed detachably and insertably in a photographic optical path between said image formation lens and said image pickup tube;

display means for displaying the fundus image and the alignment image each formed on the image pickup tube; and means for altering a characteristic of the alignment light when said variable power lens is placed in the optical path so as to maintain uniformity of the alignment image formed on the image pickup tube.

6. A fundus camera according to claim 5, wherein said means for altering a characteristic of the alignment light increases an amount of the alignment light projected when said variable power lens is disposed in the photographic optical path in order to maintain brightness of the alignment image displayed on said display means uniform.

7. A fundus camera according to claim 5, wherein said projecting means includes:

two alignment light sources;

a first pair of light guides for guiding alignment light emitted from one of said two alignment light sources, each of the first pair of light guides having a first diameter;

a second pair of light guides for guiding alignment light emitted from the other of said two alignment light sources, each of the second pair of light guides having a second diameter different from the first diameter; and a relay lens for causing alignment light emitted from any of said light guides to form an image on a periphery of the hole of said perforated mirror, the first pair of light guides emitting light when the variable power lens is in the optical path, and the second pair of light guides emitting light when the variable power lens is outside the optical path.

* * * * *